(12) United States Patent
Bäck (10) Patent No.: US 10,993,856 B2
(45) Date of Patent: May 4, 2021

(54) ARRAY OF ABSORBENT PRODUCTS

(71) Applicant: Essity Hygiene and Health Aktiebolag, Gothenburg (SE)

(72) Inventor: Lucas Bäck, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/462,380

(22) PCT Filed: Nov. 23, 2016

(86) PCT No.: PCT/SE2016/051155
§ 371 (c)(1),
(2) Date: May 20, 2019

(87) PCT Pub. No.: WO2018/097770
PCT Pub. Date: May 31, 2018

(65) Prior Publication Data
US 2019/0314223 A1   Oct. 17, 2019

(51) Int. Cl.
*A61F 13/49*   (2006.01)
*A61F 13/551*   (2006.01)
(Continued)

(52) U.S. Cl.
CPC .... *A61F 13/5519* (2013.01); *A61F 13/15747* (2013.01); *A61F 13/496* (2013.01);
(Continued)

(58) Field of Classification Search
CPC .......... A61F 13/49011; A61F 13/49012; A61F 13/49014; A61F 13/49061; A61F 13/4906;
(Continued)

(56) References Cited

U.S. PATENT DOCUMENTS 8,273,067 B2 *   9/2012   Cohen .................... A61F 13/49
604/385.01
2002/0072723 A1   6/2002   Ronn et al.
(Continued)

FOREIGN PATENT DOCUMENTS

JP   2016526981 A   9/2016

OTHER PUBLICATIONS

International Search Report and Written Opinion for International Application No. PCT/SE2016/051155, dated Jul. 3, 2017—13 pages.
(Continued)

*Primary Examiner* — Catharine L Anderson
*Assistant Examiner* — Lynne Anderson
(74) *Attorney, Agent, or Firm* — Buchanan Ingersoll & Rooney P.C.

(57) ABSTRACT

An array of products comprising three or more different sizes of disposable pant-type absorbent articles is provided, wherein each of first and second and third disposable pant-type absorbent articles comprises a chassis with a front portion and a back portion, and an absorbent body attached to the chassis, and a length direction and a width direction, wherein the size of the front and rear portion of the first disposable pant-type absorbent articles is smaller than the size of the front and rear portion of the second disposable pant-type absorbent articles, wherein the size of the front and rear portion of the third disposable pant-type absorbent articles is larger than the size of the front and rear portion of the second disposable pant-type absorbent articles, and wherein each of the front and back portions has a waist edge, a pair of leg edges and a pair of side edges and wherein a distance, in the length direction, between the leg edge of the front portion and the leg edge of the back portion, is common for all disposable pant-type absorbent articles of the array of packages when the disposable pant type absor-
(Continued)

bent articles are in a flat-out uncontracted state and said distance is measured by one of the side edges.

16 Claims, 5 Drawing Sheets

(51) Int. Cl.
 *A61F 13/15* (2006.01)
 *A61F 13/494* (2006.01)
 *A61F 13/496* (2006.01)
(52) U.S. Cl.
 CPC .. *A61F 13/49011* (2013.01); *A61F 13/49014* (2013.01); *A61F 13/49413* (2013.01); *A61F 13/55105* (2013.01); *A61F 2013/49025* (2013.01)
(58) Field of Classification Search
 CPC ............... A61F 13/496; A61F 13/551; A61F 13/55105; A61F 13/55115; A61F 13/5519; A61F 2013/49025; A61F 2013/49026; A61F 2013/49028; A61F 2013/49033; A61F 2013/49073; A61F 2013/49074
 See application file for complete search history.

(56) References Cited

U.S. PATENT DOCUMENTS

| | | |
|---|---|---|
| 2002/0148548 A1 | 10/2002 | Murie et al. |
| 2002/0151422 A1 | 10/2002 | Duhm et al. |
| 2008/0051747 A1 | 2/2008 | Cohen |
| 2013/0072887 A1* | 3/2013 | LaVon ............... A61F 13/64 604/368 |
| 2013/0110068 A1 | 5/2013 | Nelson et al. |
| 2013/0211356 A1* | 8/2013 | Nishikawa ........ A61F 13/55115 604/365 |
| 2014/0288519 A1 | 9/2014 | Schmitz et al. |
| 2014/0378932 A1 | 12/2014 | Seitz et al. |
| 2015/0065982 A1 | 3/2015 | Hamilton et al. |
| 2015/0073373 A1* | 3/2015 | Mukai ............... A61F 13/535 604/385.29 |
| 2016/0095764 A1 | 4/2016 | Seitz et al. |
| 2016/0100989 A1 | 4/2016 | Seitz et al. |
| 2016/0100997 A1* | 4/2016 | Seitz ............... A61F 13/49019 604/368 |
| 2016/0100999 A1 | 4/2016 | Hamilton et al. |
| 2016/0206485 A1 | 7/2016 | Seitz et al. |
| 2017/0079851 A1* | 3/2017 | Greening, II ....... A61F 13/5633 |

OTHER PUBLICATIONS

International Preliminary Report on Patentability for International Application No. PCT/SE2016/051155, dated Mar. 18, 2019—6 pages.
Office Action (Notice of Reasons for Rejection) dated Jul. 20, 2020, by the Japanese Patent Office in corresponding Japanese Patent Application No. 2019-527518, and an English Translation of the Office Action. (6 pages).

* cited by examiner

ARRAY OF ABSORBENT PRODUCTS

CROSS REFERENCE TO RELATED APPLICATIONS

This is a U.S. National Phase application of PCT/SE2016/051155, filed Nov. 23, 2016, the disclosure of which is incorporated herein by reference in its entirety for all purposes.

TECHNICAL FIELD

The invention relates to an array of products comprising three or more different sizes of disposable pant-type absorbent articles, the array comprises: a first package comprising a plurality of first disposable pant-type absorbent articles and a second package comprising a plurality of second disposable pant-type absorbent articles.

BACKGROUND

Disposable absorbent articles, for example in the form of incontinence liners, baby diapers and sanitary napkins, are well known. The general purpose of such absorbent articles is to absorb, distribute and store various types of body exudates, while providing a high level of comfort and sense of dryness to the wearer during use of the absorbent article. Also, such an absorbent article is configured to prevent the wearer from getting the clothes soiled by such body exudates.

Absorbent articles in the form of incontinence articles are used to protect a wearer against urine leakage. An incontinence article can be configured for example as a pant diaper, a sanitary pant or an incontinence pant adapted for use by a baby, child or adult, male or female user. Also, an incontinence article is designed with an absorption capacity which is adapted to absorb the discharges that is expected to be released into the article when it is worn. Incontinence articles are used to assist persons with incontinence so that they can maintain a normal lifestyle without any inconvenience caused by incontinence.

With regard to adult users of pant-type incontinence articles, there is a particular demand for such articles which are adapted to different sizes and shapes of the anatomy. Furthermore, there is a demand for incontinence articles which are designed in a manner so that they resemble regular underwear. In fact, adult persons who use incontinence articles may be reluctant to use articles which are "diaper-like" and which are perceived as bulky, uncomfortable and unattractive, and which may be visible if, for example, the user wears tight clothes over an incontinence article. This means that there is a desire to provide incontinence articles which are less bulky and which have a look and feel which is similar to traditional underwear.

Also, there is a desire to provide incontinence articles which are stylish and attractive for both men and women of various sizes and which follow the anatomy and body contour. In this manner, a more discreet article can be provided to the wearer.

In summary, there is a need for an assortment, or array, of incontinence articles which can be adapted in an optimal manner as regards the fit, comfort and function. Furthermore, there is a need for efficient manufacturing methods for producing such an array of articles, in particular time-consuming and costly adjustments or modifications of the manufacturing process need to be avoided, for example during a change from production of one size to another, and vice versa.

SUMMARY

An object with the present invention is to provide an array of products, which is adapted to male and female users of various sizes and which follow requirements as to comfort, fit and design but at the same time is not overly time-consuming or costly to produce. The array of products can be manufactured by means of an efficient manufacturing process that is rapidly adaptable to change from manufacturing of one size to another.

An array of products comprising three or more different sizes of disposable pant-type absorbent articles, the array comprises: a first package comprising a plurality of first disposable pant-type absorbent articles; a second package comprising a plurality of second disposable pant-type absorbent articles; a third package comprising a plurality of third disposable pant-type absorbent articles, wherein each of the first and second and third disposable pant-type absorbent articles comprises a chassis with a front portion and a back portion, and an absorbent body attached to the chassis, and a length direction and a width direction, wherein the size of the front and rear portion of the first disposable pant-type absorbent articles is smaller than the size of the front and rear portion of the second disposable pant-type absorbent articles, wherein the size of the front and rear portion of the third disposable pant-type absorbent articles is larger than the size of the front and rear portion of the second disposable pant-type absorbent articles, and wherein each of the front and back portions has a waist edge, a pair of leg edges and a pair of side edges and wherein a distance, in the length direction, between the leg edge of the front portion and the leg edge of the back portion, is common for all disposable pant-type absorbent articles of the array of packages when the disposable pant type absorbent articles are in a flat-out uncontracted state and said distance is measured by one of the side edges.

The array of products according to the disclosure provides certain advantages due to the fact that it comprises articles which, have some features in common making the whole adjustment step when changing the manufacturing process from one disposable pant type diaper to another size of a disposable pant type diaper according to the disclosure of the array of products. At the same time, by keeping this feature common for disposable pant type absorbent articles, other features can be varied without restrictions providing excellent comfort, fit and leakage security.

According to an embodiment of the array of products the extent, in the length direction, of an adhesive layer for fastening the curved elastic leg feature on the back portion is common for all disposable pant-type absorbent articles of the array of products, when the disposable pant-type absorbent articles are in a flat-out uncontracted state. This means that a manufacturing process can be implemented in a manner so that a change between production of one article size to another article size can be carried out in a simple manner by avoiding a time-consuming change and yet provide for the manufacture of products providing comfort, fit and leakage security for users in various shapes and sizes.

According to an embodiment of the array of products the first and second and third disposable pant-type absorbent articles have a common peak-to-peak distance (C) of a curved elastic leg feature on the back portion in the length direction when the disposable pant type absorbent articles are in a flat-out uncontracted state. The finding that the objects of the disclosed array of products can be achieved by keeping said feature common for the products and yet provide excellent properties regarding comfort, fit and leakage security for users in various shapes and sizes.

According to an embodiment of the array of products has an elastic leg feature of the back portion that extends along a path that runs at least partly along the leg edges of the back portion, the path being inclined to the width direction over at least a portion of the path.

According to a further embodiment of the array of products an angle between the path of the elastic leg feature of the back portion to the width direction is in the range of 3-45 degrees, specifically in the range of 5-30 degrees, and more specifically in the range of 5-20 degrees.

According to an embodiment of the array of products the elastic leg feature of the back portion extends from the side edge of the back portion towards a longitudinal centre line of the article.

Yet in accordance with an embodiment of the array of products the dimensions of the absorbent body in the length (G) direction and width (F) direction are common for all disposable pant-type absorbent articles of the array of products.

In accordance with an embodiment the array of products a distance, in the length direction, between a transverse centre line of the absorbent article and the edge of the absorbent body in the back portion, is identical in all disposable pant-type absorbent articles of the array of products.

The array of products according to any of the preceding claims, wherein the front and back portions are joined to each other at opposite side edges to at least partly define a waist-opening and a pair of leg-openings, and wherein the absorbent body is located mainly in a crotch portion of the article.

At least in one embodiment of the array of products the elastic leg feature of the back portion comprises a set of 2 to 10 individual elastic threads, specifically 3 to 8 individual elastic threads, or more specifically 3 to 6 individual elastic threads. It is a special advantage with the embodiment that a suitable number of additional threads can be applied for larger sizes by keeping the innermost threads at the same distance from one another and said suitable number of additional threads can be more towards the waist edge and applied to follow in the general direction of the waist edge contour by simply activating said suitable number of additional threads. Suitably, the individual elastic threads are located substantially parallel and offset from each other. Alternatively, the elastic leg feature comprises an elastic band.

According to one alternative embodiment the array of products at least the front and/or back portion is extensively made of an elastic web material, wherein the elastic web material is made of at least two substantially inelastic sheets of web material that are laminated together and having an elastic feature sandwiched between said at least two sheets of web material, and wherein the elastic feature is attached to the at least two sheets in a tensioned state in the width direction to provide a web material that is elasticized in the width direction.

According to an embodiment the array of products the elastic feature comprises an elastic film extending both in the length direction and width direction.

According to still another embodiment the array of products the front and back portions are made of individual parts that are mutually interconnected by means of the absorbent body.

According to yet another embodiment the array of products the elastic leg feature of the back portion extends from the side edge of the back portion towards a longitudinal centre line of the article.

According to an embodiment the array of products an external marking is provided on a package indicating the size of the disposable pant-type absorbent articles therein.

More specifically the array of products is selected from a group of disposable pant-type diapers or sanitary pants or incontinence pants. Furthermore, the above-mentioned object of the invention is obtained by means of a method for manufacturing an array of disposable pant-type absorbent articles.

BRIEF DESCRIPTION OF THE DRAWINGS

The invention will be described in greater detail below with reference to the figures shown in the appended drawings.

DETAILED DESCRIPTION OF PARTICULAR EMBODIMENTS

Different aspects of the present disclosure will be described more fully hereinafter with reference to the enclosed drawings. The embodiments disclosed herein can, however, be realized in many different forms and should not be construed as being limited to the aspects set forth herein.

Figure 1:
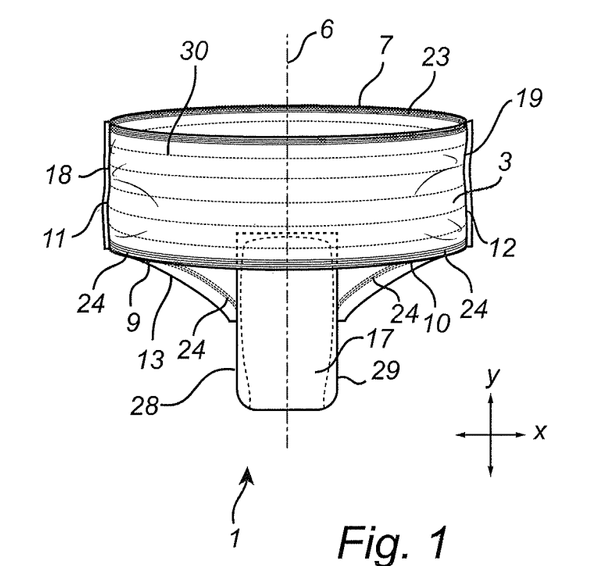
FIG. 1 shows a perspective front view of the absorbent article according to the disclosure.

With reference to FIG. 1 of the drawings, there is shown an embodiment of a disposable pant-type absorbent article 1 illustrated in an assembled and ready-to-use state. An alternative absorbent article 1 is shown in FIG. 2.

The disclosure relates to an array of disposable absorbent articles and the article 1 shown in FIG. 1 is not intended to describe a specific model, but is used to describe the general principles of an absorbent article.

Figure 2:
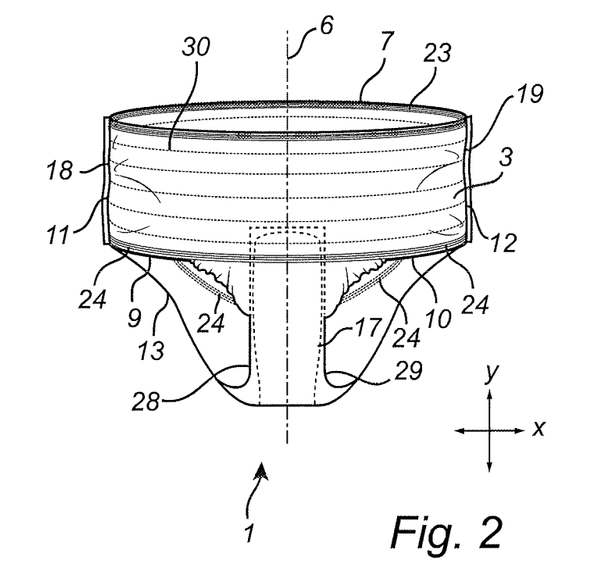
FIG. 2 shows a perspective front view of an alternative embodiment of the absorbent article.

With reference to FIG. 1 and FIG. 2, the pant-type absorbent article 1 is for example in the form of a pant diaper, a sanitary pant or an incontinence pant adapted for use by a baby, child or adult, male or female user. The pant-type absorbent article 1 according to FIG. 1 comprises a H-type design of absorbent article and FIG. 2 comprises a single-piece chassis 2 having a front portion 3, a back portion 4, a crotch portion 5 connecting the front and back portions 3, 4, and a centre line 6 in the longitudinal direction of the article. The absorbent article 1 has a longitudinal direction, a transverse direction and a thickness direction.

With reference to FIG. 1 the front portion 3 has a waist edge 7, a pair of leg edges 9, 10 and a pair of side edges 11, 12. Furthermore, the back portion 4 has a waist edge 8, a pair of leg edges 13, 14 and a pair of side edges 15, 16.

As mentioned above, the absorbent article 1 comprises a crotch portion 5, which comprises an absorbent body 17 located mainly in said crotch portion 5. The absorbent body 17 may be manufactured separately from the chassis 2 and inserted and fastened to the chassis 2 at a suitable manufacturing step. This process will be described in greater detail below.

The side edges 11, 12 of the front portion 3 are attached to the opposite side edges 15, 16 of the back portion 4 by means of permanent or re-closable side connections 18, 19 such as side seams, hook and loop fasteners, adhesive fasteners, or the like, in order to at least partly define a waist opening 20 and a pair of leg openings 21, 22.

A first elastic element in the form of an elastic waist component 23 is fastened to the chassis 2 at least partly along the waist edges 7, 8 forming part of the front portion 3 and the back portion 4. The purpose of the elastic waist component 23 is to provide the absorbent article 1 with a good fit around the waist of the user wearing the article. The elastic waist component 23 is fastened relatively close to the waist edges 7, 8, around the waist opening 20.

Furthermore, a second elastic element in the form of an elastic leg component 24 is fastened to the chassis 2 at least partly along the leg edges 9, 10 of the front portion 2 for the purpose of providing the absorbent article 1 with a good fitting around the legs of the user wearing the article. The elastic leg component 24 is fastened relatively close to the leg edges 9, 10, 13, 14.

Figure 4:
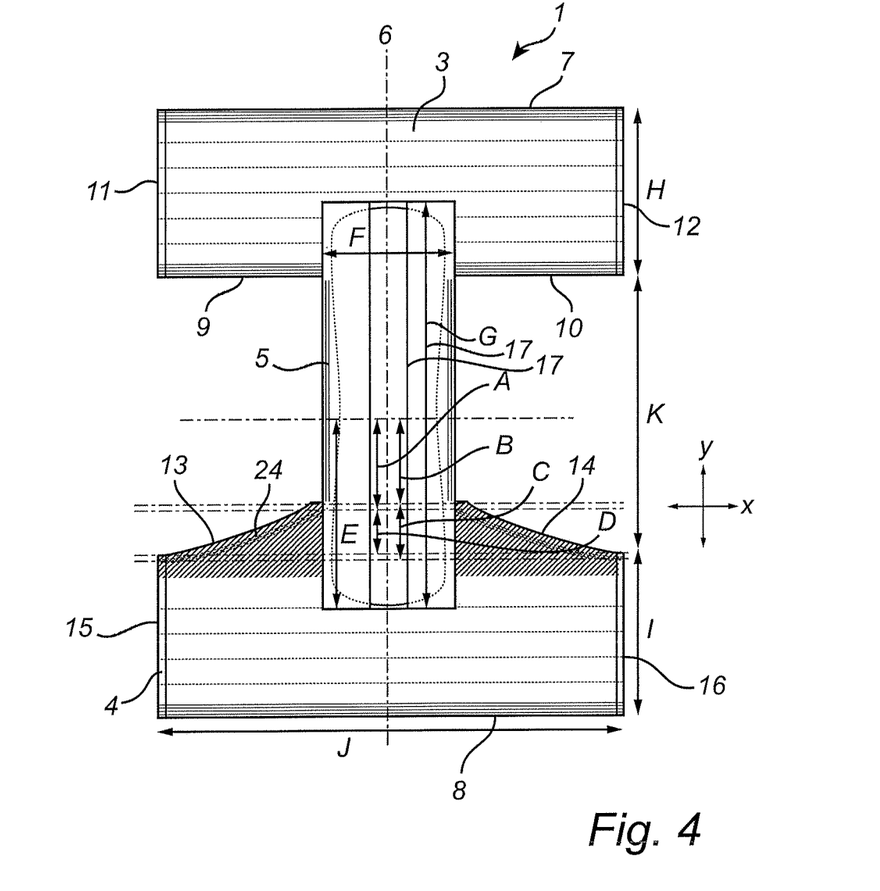
FIG. 4 shows a plan view of an embodiment of the absorbent article according to the disclosure when the absorbent article is in a flat-out uncontracted state.

As shown in particular in FIG. 4, the elastic leg component 24 forms a straight line in the front portion 3 and has a curved configuration in the back portion 4.

Furthermore, a first absorbent body elastic and a second absorbent body elastic are arranged along the crotch portion 5. The first absorbent body elastic is arranged along a first crotch edge 28 whereas the second absorbent body elastic is arranged along a second crotch edge 29. In particular, the first absorbent body elastic and the second absorbent body elastic are arranged relatively close to the longitudinal crotch edges 28, 29. In a similar manner, the elastic waist component 23 and the elastic leg component 24 are also arranged relatively close to the waist edges 7, 8 and the leg edges 9, 10, 13, 14 respectively, as shown in FIG. 1 and FIG. 2.

If the elastic leg component 24 and the elastic waist component 23 are fastened at a location close to the waist and leg edges 7, 8, 9, 10, 13, 14 respectively, less non-elasticised web material is available at the leg and waist edges such that less frills is created along said edges. This is an advantage, since a large amount of material at the leg edges may be perceived as uncomfortable by a user and may give the user an impression that the article is not similar to conventional underwear.

Having the elastic leg feature 24 positioned closer to the leg edge 9, 10 may also result in an absorbent article 1 having an improved fit which corresponds to the shape of the legs of the user. It is thus desirable to provide an elasticised leg edge 9, 10 of the front and back portion 3, 4 that has a more cuff like appearance with less frills, thereby providing the absorbent article 1 with an appearance more similar to cloth underwear.

Furthermore, as shown in FIG. 1 and FIG. 2, the absorbent article 1 comprises a front elastic component 30 and a back elastic component (not shown) which are both based on a number of elastic threads mounted at a certain distance from each other in a generally parallel manner around the article 1, i.e. the region of the belly and the backside of the user. The purpose of these elastic components 30 . . . is to contribute to a good fit and comfort for the wearer of the article 1. In particular, the configuration of the elastic threads can be adapted to the need for a suitable fit and comfort for male and female users of the article 1.

This disclosure is based on the principle that the positioning of the elastic threads and also the elastic properties of the elastic threads can be individually adapted so as to provide a configuration of the back elastic component and front elastic component 30 which is arranged so as to individually fit various anatomies, respectively while still keep many features common in order to facilitate and allow for easier manufacturing. More precisely, the positioning of the elastic threads refers to the manner, in which the threads are laid out, in a geometric sense, along the absorbent articles in the array and the distance between any two adjacent elastic threads.

Figure 3:
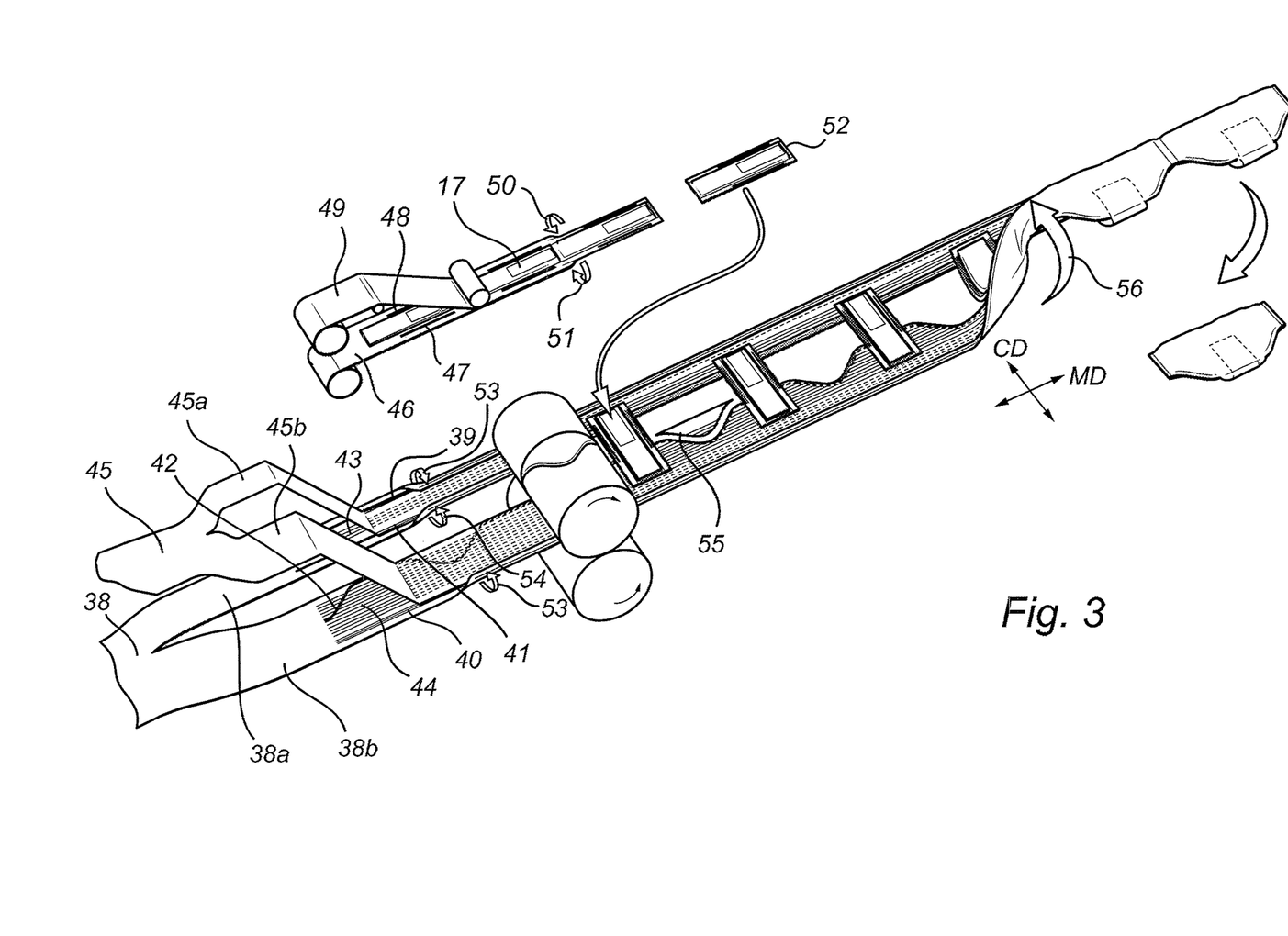
FIG. 3 shows a schematic illustration of a manufacturing process for an absorbent article according to the disclosure.

Furthermore, and with reference to FIG. 3 and as mentioned above, it can be noted that a process of fastening the elastic waist component 23 and the elastic leg component 24 close to an edge of a web material, i.e. in this case close to the waist edges 7, 8 and the leg edges 9, 10, 13, 14 respectively, is difficult due to the manufacturing tolerances of the production line. The provision of elastic elements along the edges of the article, i.e. along the waist, legs and crotch edges, contributes to a well-fitting absorbent article such as an incontinence article. Such elastic elements are normally provided with a number of elastic threads which are arranged along a waist edge, a leg edge and two crotch edges.

A production process for a pant-type absorbent article operates at a high rate and such a fully automated manufacturing line needs to have a certain tolerance. If the elastic threads of the elastic components are positioned too close to the corresponding edges, there is a risk that the threads may actually be laid and positioned outside the edges. Since glue is normally applied to the threads, there is a risk for production interruption if the elastic threads are erroneously positioned outside the actual edges of the article.

In a manner which is conventional as such, the absorbent article 1 comprises a liquid permeable topsheet, i.e. a sheet which is intended to face the user of the article 1, and a liquid impermeable backsheet, i.e. a sheet which is placed so as to face the garment worn by the user. Generally, the liquid permeable topsheet 32 comprises or consist of a nonwoven material. The topsheet material may further be composed of tow fibres, porous foams, apertured plastic films and similar materials. The materials suited as topsheet materials should be soft and non-irritating to the skin and should be readily penetrated by body fluid, e.g. urine or menstrual fluid, and display low rewetting properties.

Furthermore, the liquid impermeable backsheet may consist of a thin plastic film, e. g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent article, while still preventing liquids from passing through the backsheet material.

According to various embodiments, the materials which can be used for manufacturing the backsheet include thin and flexible fluid impermeable plastic films, or fluid impermeable nonwoven materials, fluid impermeable, foams and fluid impermeable laminates.

Furthermore, the backsheet is formed by a single layer, and can alternatively be formed by a multi-layered structure, i.e. a laminate, wherein at least one layer is fluid impermeable. Furthermore, the backsheet can optionally be elastic in either direction. According to further embodiments, the backsheet may be breathable, implying that air and vapor may pass through the backsheet. Furthermore, the backsheet may optionally have an outer, garment-facing surface of a textile material such as nonwoven.

The absorbent core 17 can be formed by a single layer consisting of fibres of cellulosic fluff pulp. According to alternative embodiments, the absorbent core 17 can be made up of any suitable absorbent or fluid-absorbing material as known in the art, for example foam, fiber waddings and similar materials.

Furthermore, the absorbent core 17 may consist of a mixture of cellulosic fluff pulp and a suitable amount of superabsorbent particles. Such superabsorbent material is well known in the field of absorbent articles, and is constituted by a water-swellable and water-insoluble material, which is capable of absorbing large quantities of fluid upon formation of a hydrogel. Normal superabsorbent materials are capable of absorbing fluids of at least 10 times its own weight.

According to further embodiments, the absorbent core 17 may further incorporate components for improving the properties of the absorbent core. Some examples of such components are binder fibers, fluid-dispersing materials, fluid acquisition materials, etc. as known in the art. The absorbent core 17 may also be a homogeneous structure or may be a layered structure with laminates of the same or different materials. The absorbent layers may have uniform thickness or may vary in thickness in different parts of the layers.

The topsheet and backsheet may be connected to each other for example by adhesive bonding, gluing or welding by heat or ultrasonic. The topsheet and/or the backsheet may further be attached to the absorbent body by any method known in the art, such as adhesive, heat-bonding etc.

According to an embodiment, the topsheet and backsheet in the portions forming the front portion 3 and the back portion 4 may be of different type than the topsheet and backsheet in the crotch portion 5. In the latter case, it is suitable with a fluid-permeable topsheet and a fluid-impermeable backsheet (as described above) since the absorbent article 1 of this embodiment must have absorbent properties in the crotch portion 5. However, in the parts forming the front portion 3 and the back portion 4, both the topsheet and the backsheet may be for example liquid-impermeable, since these parts of the absorbent article 1 generally do not need to have absorbent properties.

Also, as mentioned initially, there is a requirement for producing absorbent articles which are similar to conventional underwear, i.e. having a look and feel corresponding to normal male and female underwear and which are adapted to male and female users. Consequently, there are requirements to provide an array, or a set, of gender-specific absorbent articles which are customized for male and female users, respectively, while still allowing an efficient manufacturing process, substantially without any time-consuming and costly modifications of the manufacturing process, for example during a change from production of a male article to a female article.

As mentioned, the positions and the elastic properties of at least the elastic threads forming the front elastic component and the back elastic component can be varied in order to provide articles which are adapted to the various anatomies and to other requirements regarding absorbent products. An example embodiment of a manufacturing line for a pant-type absorbent article 1 is schematically illustrated in FIG. 3. A first continuous sheet 38 of web material is supplied and is also divided, in a lengthwise manner, so as to form a first web section 38a and a second web section 38b. The first web section 38a forms the basis of a backsheet for the front portion 3 of the absorbent article 1, whereas the second web section 38b forms the basis of a backsheet for the back portion 4.

A plurality of strips of elastic material are attached to the first and second web sections 38a, 38b in a tensioned state. More precisely, a first strip 39 and a second strip 40 of elastic material form the basis of the elastic waist component 23, and a third strip 41 and a fourth strip 42 of elastic material form the basis of the elastic leg component 24. Also, a fifth strip 43 and a sixth strip 44 of elastic material form the basis of the front elastic component 30 and the back elastic component 31, respectively.

The strips 39, 40, 41, 42, 43, 44 of elastic material may be glued or otherwise fastened to the continuous sheets 38a, 38b of web material, and said strips are intended to form an elastic web feature of the absorbent article 1 as described above with reference to FIGS. 1 and 2.

Next, a further continuous sheet 45 of web material is provided and is split longitudinally in order to form a third web section 45a and a fourth web section 45b. The third web sections 45a forms the basis of a topsheet for the front portion 3 whereas the fourth web section 45b forms the basis of a topsheet for the back section 4.

The third web section 45a and the fourth web section 45b are joined to the first web section 38a and the second web section 38b, respectively, in order to form a laminated product having the strips 39, 40, 41, 42, 43, 44 of elastic material sandwiched between the first web section 38a and the third web section 45a, and also between the second web section 38b and the fourth web section 45b. The second sheets may be attached to each other by ultrasonic bonding, welding, adhesive, embossing, mechanical fastening, or the like. The attachment of the above-mentioned web sections and elastic strips is here described as being performed in consecutive steps but these steps are typically performed in a single step.

In order to form the crotch portion 5 (see FIG. 1) with its absorbent core 17, a third continuous sheet 46 of web material is provided and forms the basis of a backsheet for the crotch portion 5. The absorbent core 17 is then laid out on the third continuous sheet 46. Also, a seventh strip 47 and an eighth strip 48 of elastic material are also laid out on the third sheet 46 of web material. The seventh strip 47 of elastic material forms the basis of the first absorbent body elastic 25 (see FIGS. 1a and 2), whereas the eighth strip 48 of elastic material forms the basis of the second absorbent body elastic 26.

Next, a fourth continuous sheet 49 of web material is provided and is joined to the third continuous sheet 46, suitably in a manner which is similar to that described above with reference to the first web section 38a, the second web section 38b, the third web section 45a and the fourth web section 45b. During this process, the seventh strip 47 and eighth strip 48 of elastic material, as well as the absorbent core 17, are sandwiched between said third continuous sheet 46 of web material and said fourth continuous sheet 49 of web material.

In order to adapt the manufacturing process to a male-type article and a female-type article, respectively, the process can be modified by choosing suitable elastic material (i.e. for the strips 39, 40, 41, 42, 43, 44 of elastic material) to be included in the articles. Such selections of elastic material according to dimensions, brand, elastic properties and other parameters must be considered to be implemented in the manufacturing process in an efficient manner generally without any interruptions or time-consuming modifications.

A folding procedure is next carried out so as to fold the edges of the crotch portion 5 and form the edges 36, 37 on the crotch portion 5. This folding operation is indicated in a simplified manner with the arrows 50 and 51 in FIG. 3. Similarly, folding of the front portion 3 and the back portion 4 is indicated in FIG. 3 with arrows 53, 54 in a simplified manner.

In a further manufacturing step, the web formed by means of the third sheet 46 of web material, the fourth sheet 49 of web material 49 and the absorbent core 17, is cut into individual pieces 52, each of which forms the above-mentioned crotch portion 5 which is subsequently attached to the web formed by the first and second web sections 38a, 38b and the third and fourth web sections 45a, 45b. In this regard, the crotch portions 5 are laid out at a predetermined distance so as to bridge the front portion 3 and the back portion 4 and to form the basis of the finished absorbent article. As shown in FIG. 3, a piece 52 which forms a crotch portion 5 is laid out in a transversal direction in relation to the webs forming the front portion and the back portion.

The crotch portion 5 may be attached to the chassis using any known fastening technology, such as ultrasonic bonding, welding, adhesive, embossing, mechanical fastening, or the like. In this manner, a complete chassis is formed for the article 1 in question.

In a subsequent manufacturing step, leg openings 55 are cut out of the laminated web material forming the chassis of finished absorbent articles. The cutting may be performed by any type of suitable cutting equipment (not shown in FIG. 3), such as rolling cutting using two opposite rollers.

Next, the first and fourth web sections 38b, 45b are folded to form the final product, such that the first web section 38b becomes a backsheet of the chassis and the fourth web section 45b becomes the topsheet of the chassis. This folding is shown with an arrow 56 in FIG. 3. After for example welding of side seams, the continuous assembly of products is cut into individual absorbent articles by means of cutting equipment (not shown in FIG. 3).

The array of products according to the disclosure provides certain advantages due to the fact that it comprises articles which have some features in common making the whole adjustment step when changing the manufacturing process from one disposable pant type diaper to another size of a disposable pant type diaper according to the disclosure of the array of products. At the same time, by keeping this feature common for disposable pant type absorbent articles, other features can be varied without restrictions providing excellent comfort, fit and leakage security.

According to an embodiment as illustrated in FIG. 4 of the array of products 1 the extent (E), in the length direction, of an adhesive layer for fastening the curved elastic leg feature 24 on the back portion 4 is common for all disposable pant-type absorbent articles 1 of the array of products, when the disposable pant-type absorbent articles are in a flat-out uncontracted state. The flat out uncontracted state can be achieved by release the side seams and open up the product and put on an even surface. Applying about 40-45 N will put the product in an uncontracted state in that the elastics is stretched to a threshold when the non-woven material of the product is holding the shape and form of the product. More information and data about an absorbent article as in.

This means that a manufacturing process can be implemented in a manner so that a change between production of one article size to another article size can be carried out in a simple manner by avoiding a time-consuming change and yet provide for the manufacture of products providing comfort, fit and leakage security for users in various shapes and sizes.

Figures 5A, 5B:
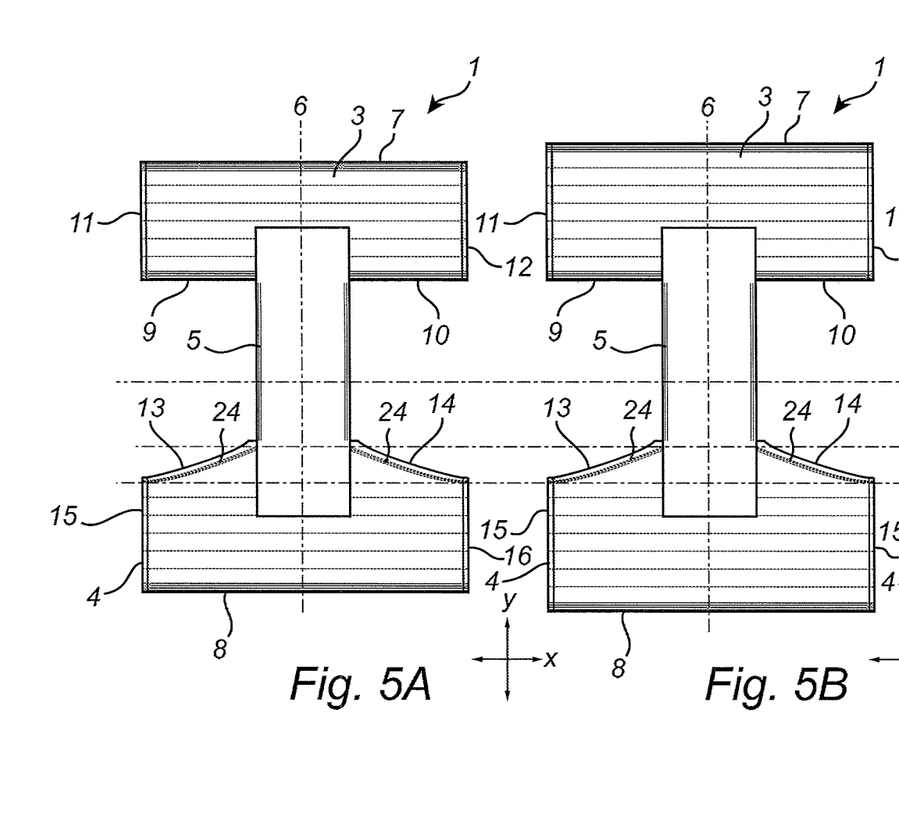
FIGS. 5a-c show a plan view of an embodiment of the array of products according to the disclosure when the absorbent articles are in a flat-out uncontracted state.
Figure 5C:
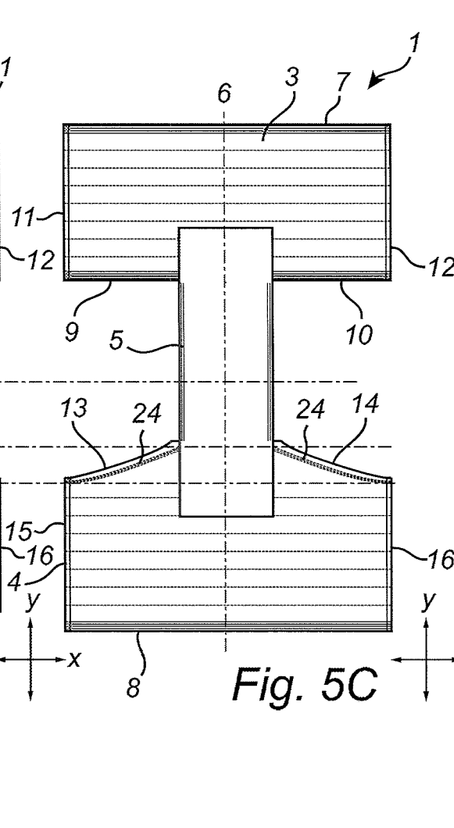

According to an embodiment in FIG. 4 and more clearly illustrated in FIGS. 5a-5c the first and second and third disposable pant-type absorbent articles have a common peak-to-peak distance (C) of a curved elastic leg feature on the back portion in the length direction when the disposable pant type absorbent articles are in a flat-out uncontracted state. The finding that the objects of the disclosed array of products can be achieved by keeping said feature common for the products and yet provide excellent properties regarding comfort, fit and leakage security for users in various shapes and sizes.

According to an embodiment of the array of products has an elastic leg feature of the back portion that extends along a path that runs at least partly along the leg edges of the back portion, the path being inclined to the width direction over at least a portion of the path.

According to an embodiment, a manufacturing process in which a change between production of product of various sizes must otherwise be carried out can be made by simply switching the elastic threads adapted for a one article for other elastic threads (having other dimensions or elastic properties) adapted for a second article. Alternatively, the number of threads can be changed during such an operation.

According to an embodiment of the array of products has an elastic leg feature of the back portion that extends along a path that runs at least partly along the leg edges of the back portion, the path being inclined to the width direction over at least a portion of the path.

According to a further embodiment of the array of products an angle between the path of the elastic leg feature of the back portion to the width direction is in the range of 3-45 degrees, specifically in the range of 5-30 degrees, and more specifically in the range of 5-20 degrees.

According to an embodiment of the array of products the elastic leg feature of the back portion extends from the side edge of the back portion towards a longitudinal centre line of the article.

Yet in accordance with an embodiment of the array of products the dimensions of the absorbent body in the length (G) direction and width (F) direction are common for all disposable pant-type absorbent articles of the array of products.

In accordance with an embodiment the array of products a distance, in the length direction, between a transverse centre line of the absorbent article and the edge of the absorbent body in the back portion, is identical in all disposable pant-type absorbent articles of the array of products.

Figure 6:
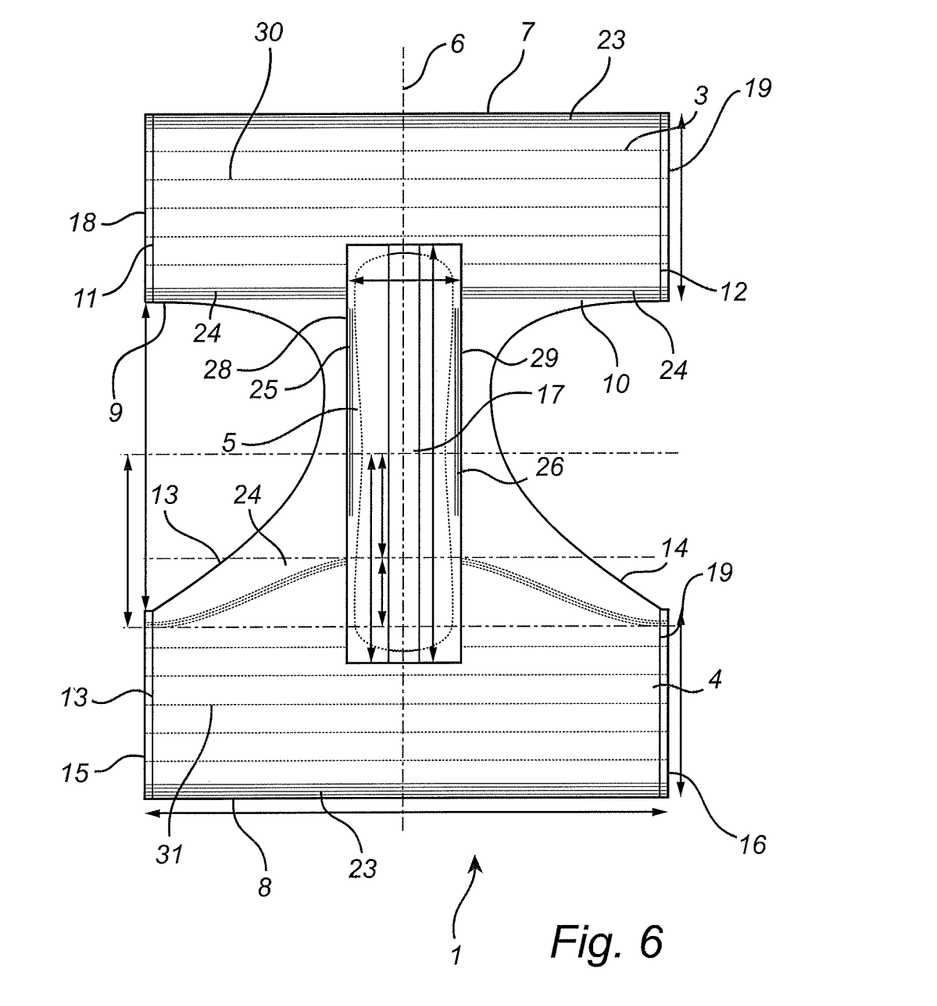
FIG. 6 is a plan view of the absorbent article of FIG. 2

In FIG. 6 an alternative embodiment of a product of the array of products is disclosed, wherein the front and back portions are joined to each other or formed by one chassis and then side edges are closed so as to at least partly define a waist-opening and a pair of leg-openings, and wherein the absorbent body is located mainly in a crotch portion of the article. The resulting product is similar to the embodiment of FIG. 2 and is more described in the above sections relating to said embodiment.

At least in one embodiment of the array of products the elastic leg feature of the back portion comprises a set of 2 to 10 individual elastic threads, specifically 3 to 8 individual elastic threads, or more specifically 3 to 6 individual elastic threads. It is a special advantage with the embodiment that a suitable number of additional threads can be applied for larger sizes by keeping the innermost threads at the same distance from one another and said suitable number of additional threads can be more towards the waist edge and applied to follow in the general direction of the waist edge contour by simply activating said suitable number of additional threads. Suitably, the individual elastic threads are located substantially parallel and offset from each other. Alternatively, the elastic leg feature comprises an elastic band.

According to one alternative embodiment the array of products (not shown) at least the front and/or back portion is extensively made of an elastic web material, wherein the elastic web material is made of at least two substantially inelastic sheets of web material that are laminated together and having an elastic feature sandwiched between said at least two sheets of web material, and wherein the elastic feature is attached to the at least two sheets in a tensioned state in the width direction to provide a web material that is elasticized in the width direction.

According to an embodiment the array of products the elastic feature comprises an elastic film extending both in the length direction and width direction.

According to yet another embodiment the array of products the elastic leg feature of the back portion extends from the side edge of the back portion towards a longitudinal centre line of the article.

According to an embodiment the array of products (not shown) an external marking is provided on a package indicating the size of the disposable pant-type absorbent articles therein.

The invention is not limited to the embodiment but can be varied within the scope of the appended claims. For example, the principles of the present invention are equally applicable to any type of hygienic absorbent article. Such articles include various types of incontinence liners and pads, and also sanitary napkins, menstrual pads, panty liners or similar products which are worn inside a supporting panty or which a holder. Such articles also include baby diapers with tape fasteners, pant diapers, training pants, belted diapers or similar disposable absorbent garments.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive. It should be understood that the present absorbent articles and its components and methods are not intended to be limited to the particular forms disclosed. Rather, they are intended to include all modifications, equivalents, and alternatives falling within the scope of the claims. They are further intended to include embodiments that may be formed by combining features from the disclosed embodiments, and variants thereof.

The invention claimed is:

1. An array of products comprising three or more different sizes of disposable pant-type absorbent articles for adult users, the array comprising:
 a first package comprising a plurality of first disposable pant-type absorbent articles;
 a second package comprising a plurality of second disposable pant-type absorbent articles; and
 a third package comprising a plurality of third disposable pant-type absorbent articles,
 wherein:
  each of the first and second and third disposable pant-type absorbent articles comprises a chassis with a front portion and a back portion, and an absorbent body attached to the chassis, and a length direction and a width direction;
  the front and back portions are made of individual parts that are mutually interconnected by means of the absorbent body;
  the back portion comprises a curved leg elastic member;
  the size of the front and back portions of the first disposable pant-type absorbent articles is smaller than the size of the front and back portions of the second disposable pant-type absorbent articles; and
  the size of the front and back portions of the third disposable pant-type absorbent articles is larger than the size of the front and back portions of the second disposable pant-type absorbent articles, and wherein each of the front and back portions has a waist edge, a pair of leg edges and a pair of side edges and wherein a distance, in the length direction, between the leg edge of the front portion and the leg edge of the back portion, is common for all disposable pant-type absorbent articles of the array of packages when the disposable pant type absorbent articles are in a flat-out uncontracted state and said distance is measured by one of the side edges, and
 wherein:
  the extent, in the length direction, of an adhesive layer for fastening the curved leg elastic member on the back portion is common for all disposable pant-type absorbent articles of the array of products, when the disposable pant type absorbent articles are in the flat-out uncontracted state; and/or
  the first and second and third disposable pant-type absorbent articles have a common peak-to-peak distance of the curved leg elastic member on the back portion in the length direction when the disposable pant type absorbent articles are in the flat-out uncontracted state.

2. The array of products according to claim 1, wherein the curved leg elastic member feature of the back portion extends along a path that runs at least partly along the leg edges of the back portion, the path being inclined to the width direction over at least a portion of the path.

3. The array of products according to claim 2, wherein an angle between the path of the curved leg elastic member of the back portion to the width direction is in the range of 3-45 degrees.

4. The array of products according to claim 1, wherein the curved leg elastic member of the back portion extends from the side edge of the back portion towards a longitudinal centre line of the article.

5. The array of products according to claim 1, wherein the dimensions of the absorbent body in the length direction and width direction are common for all disposable pant-type absorbent articles of the array of products.

6. The array of products according to claim 1, wherein a distance, in the length direction, between a transverse centre line of the absorbent article and the edge of the absorbent body in the back portion, is identical in all disposable pant-type absorbent articles of the array of products.

7. The array of products according to claim 1, wherein the front and back portions are joined to each other at opposite side edges to at least partly define a waist-opening and a pair of leg-openings, and wherein the absorbent body is located mainly in a crotch portion of the article.

8. The array of products according to claim 1, wherein the curved leg elastic member of the back portion comprises a set of 2 to 10 individual elastic threads.

9. The array of products according to claim 8, wherein the individual elastic threads are located substantially parallel and offset from each other.

10. The array of products according to claim 1, wherein the curved leg elastic member comprises an elastic band.

11. The array of products according to claim 1, wherein at least the front and/or back portion is extensively made of an elastic web material, wherein the elastic web material is made of at least two substantially inelastic sheets of web material that are laminated together and having an elastic feature sandwiched between said at least two sheets of web material, and wherein the elastic feature is attached to the at least two sheets in a tensioned state in the width direction to provide a web material that is elasticized in the width direction.

12. The array of products according to claim 11, wherein the elastic feature comprises an elastic film extending both in the length direction and width direction.

13. The array of products according to claim 1, wherein an external marking is provided on a package indicating the size of the disposable pant-type absorbent articles therein.

14. The array of products according to claim 1, wherein disposable pant-type absorbent articles are pant diapers or sanitary pants or incontinence pants.

15. An array of products comprising three or more different sizes of disposable pant-type absorbent articles for adult users, the array comprising:
   a first package comprising a plurality of first disposable pant-type absorbent articles;
   a second package comprising a plurality of second disposable pant-type absorbent articles; and
   a third package comprising a plurality of third disposable pant-type absorbent articles, wherein (1) each of the first and second and third disposable pant-type absorbent articles comprises a chassis with a front portion and a back portion, and an absorbent body attached to the chassis,
(2) the front and back portions are made of individual parts that are mutually interconnected by means of the absorbent body,
(3) the back portion comprises a curved leg elastic member,
(4) the size of the front and rear portion of the first disposable pant-type absorbent articles is smaller than the size of the front and rear portion of the second disposable pant-type absorbent articles,
(5) the size of the front and rear portion of the third disposable pant-type absorbent articles is larger than the size of the front and rear portion of the second disposable pant-type absorbent articles,
(6) each of the front and back portions has a waist edge, a pair of leg edges and a pair of side edges,
(7) a distance, in the length direction, between the leg edge of the front portion and the leg edge of the back portion, is common for all disposable pant-type absorbent articles of the array of packages when the disposable pant type absorbent articles are in a flat-out uncontracted state and said distance is measured by one of the side edges, and
(8) the extent, in the length direction, of an adhesive layer for fastening the curved leg elastic member on the back portion is common for all disposable pant-type absorbent articles of the array of products, when the disposable pant type absorbent articles are in the flat-out uncontracted state.

16. The array of products according to claim 15, wherein the first and second and third disposable pant-type absorbent articles have a common peak-to-peak distance of the curved leg elastic member on the back portion in the length direction when the disposable pant type absorbent articles are in the flat-out uncontracted state.

* * * * *